United States Patent
Sciaino, Jr.

[11] Patent Number: 5,972,006
[45] Date of Patent: Oct. 26, 1999

[54] BUCKLE SECURING MEANS FOR STERNUM BANDING ASSEMBLY

[75] Inventor: Bartolo Sciaino, Jr., Glen Rock, N.J.

[73] Assignee: Stony Brook Surgical Innovations, Inc., Northport, N.Y.

[21] Appl. No.: 08/744,970

[22] Filed: Jan. 28, 1997

[51] Int. Cl.[6] .................................................. A61B 17/08
[52] U.S. Cl. .................... 606/151; 606/151; 606/74; 606/157; 606/139
[58] Field of Search ............... 606/74, 151, 157, 606/139, 213, 215, 216, 218; 24/186, 187, 192, 20 R, 23 B, 23 W, 23 EE

[56] References Cited

U.S. PATENT DOCUMENTS

| | | | |
|---|---|---|---|
| 817,464 | 4/1906 | Barabasz | 24/186 |
| 3,000,433 | 9/1961 | Kemper | 24/23 W |
| 4,201,215 | 5/1980 | Crossett et al. | |
| 4,380,096 | 4/1983 | Nishida et al. | 24/20 R |
| 4,535,764 | 8/1985 | Ebert | |
| 4,730,615 | 3/1988 | Sutherland et al. | |
| 4,813,416 | 3/1989 | Pollak et al. | |
| 4,991,266 | 2/1991 | Oetiken | |
| 5,330,489 | 7/1994 | Green et al. | 606/151 |
| 5,356,417 | 10/1994 | Golds | 606/151 |
| 5,437,685 | 8/1995 | Blasnik | |
| 5,571,105 | 11/1996 | Gundolf | 606/74 |

*Primary Examiner*—Michael Buiz
*Assistant Examiner*—Tina T. D. Pham
*Attorney, Agent, or Firm*—Robert L. Epstein; Harold James; James & Franklin

[57] ABSTRACT

A banding assembly has a needle at one end, a long thin band, and a buckle at the other end. The buckle is provided with upstanding elements on either side of a channel which receives the band. The elements have openings adapted to be engaged by a towel clamp to retain the buckle as the band is drawn through the channel and locks into position. Once locked into place, the band is trimmed, leaving a tail extending from the buckle which is bent and "snap fits" between the elements which are then crimped over the tail. In order to withstand the high force applied on the buckle by the towel clamp as the band is positioned, the buckle is secured to the end of the band by spaced elements which extend through openings in the band and are crimped toward each other. Extending from the end of the band are spaced tabs which are bent around the rear edge of the buckle. The recess between the tabs preferrably forms one of the element receiving openings.

14 Claims, 5 Drawing Sheets

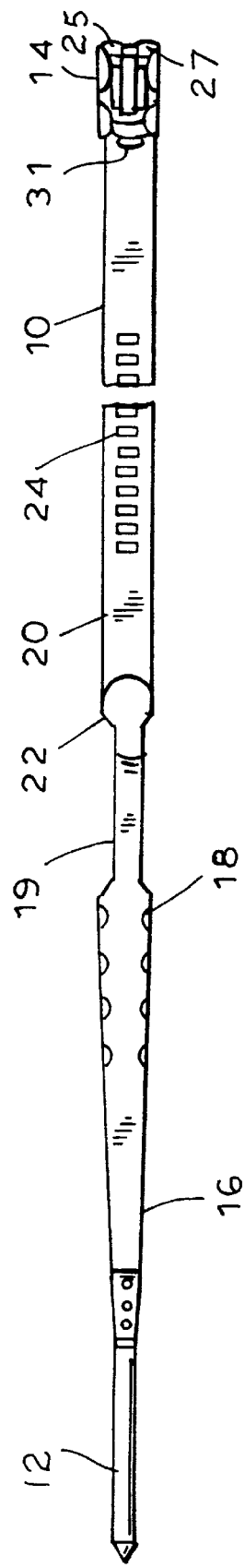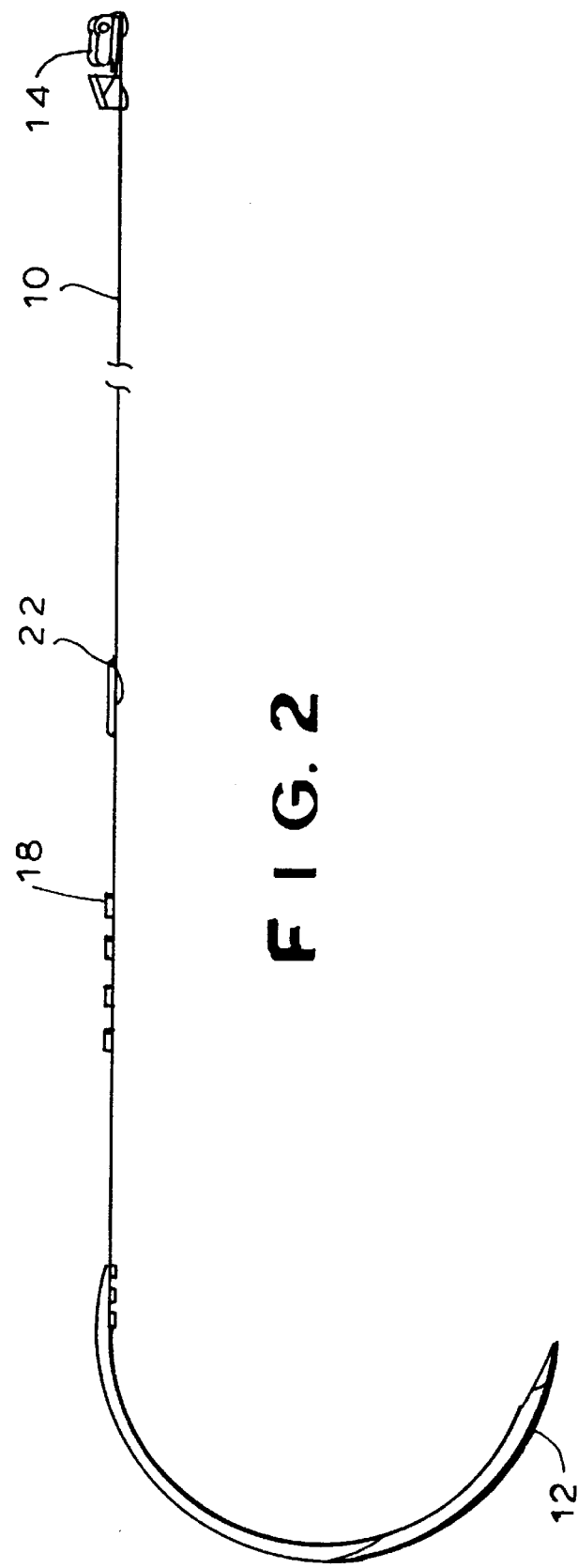

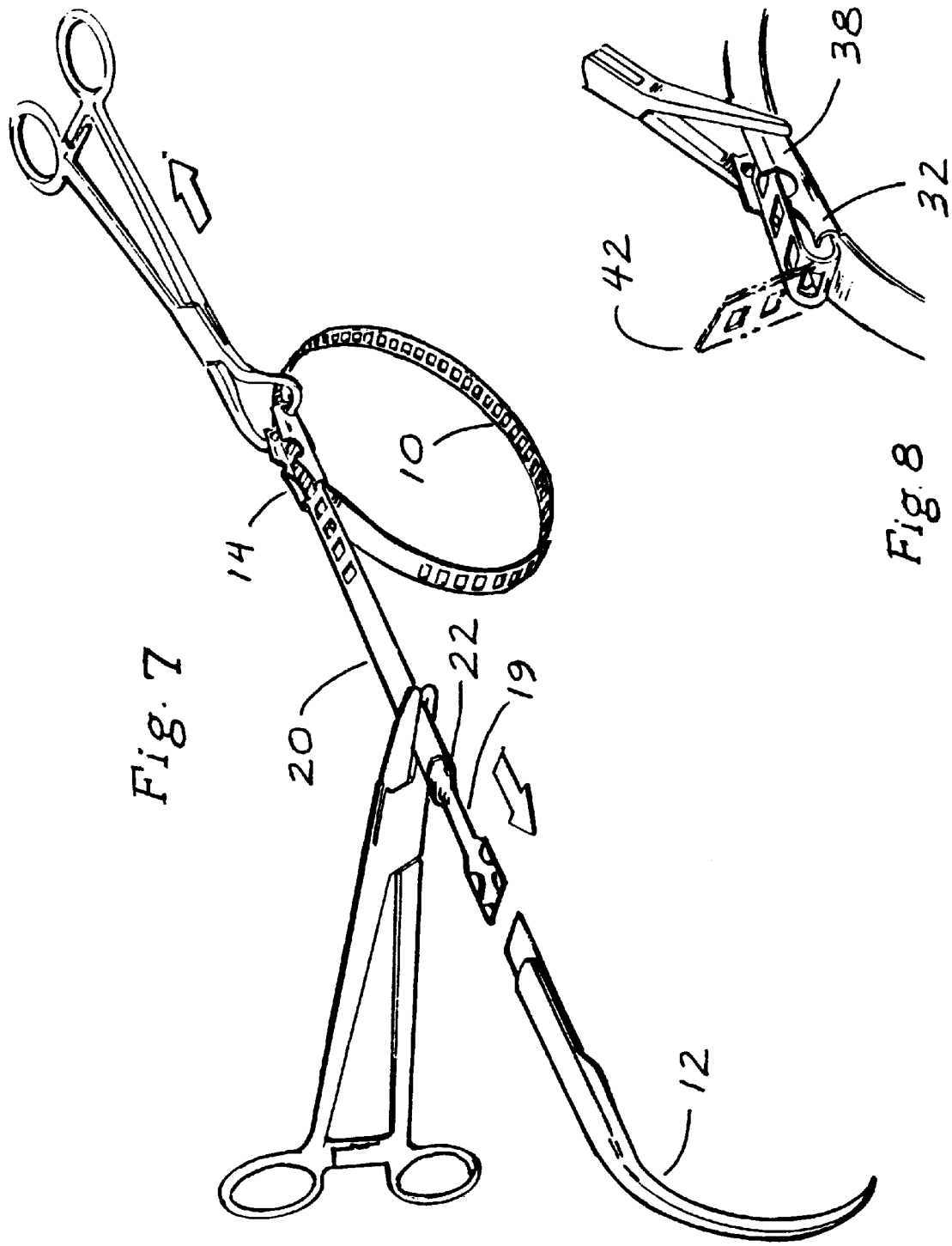

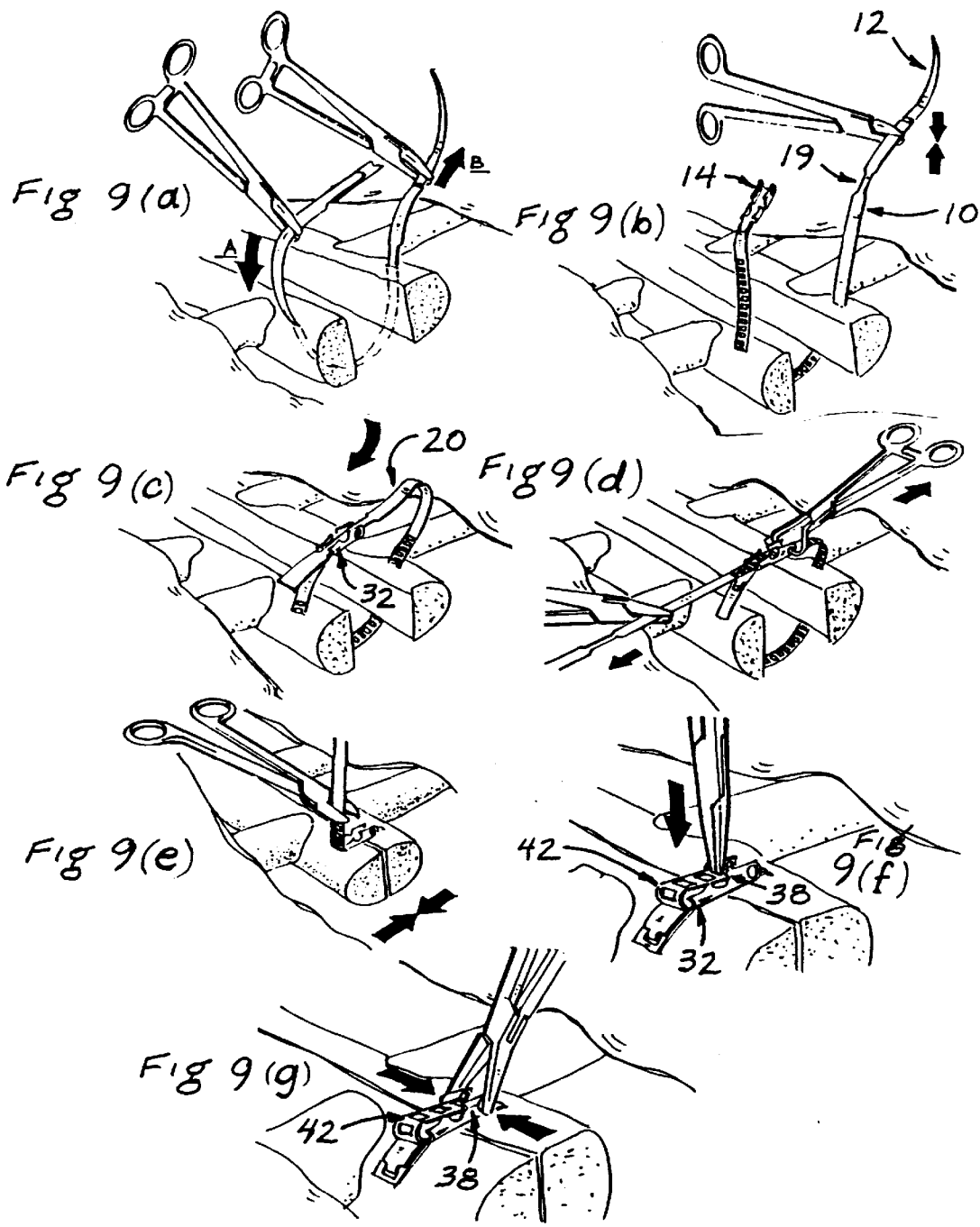

BUCKLE SECURING MEANS FOR STERNUM BANDING ASSEMBLY

The present invention relates to surgical devices and more particularly to buckle securing means for a banding assembly for clamping and closing the split halves of the sternum as part of surgery which involves a median sternotomy, such as open heart surgery.

For proper healing of the split sternum, the surgically opened faces must be approximated, compressed and held together rigidly. This task is complicated by the physiological role of the sternum. The sternum is a functional component of the thoracic cage which, with the costal cartilages, serves as the hinge for the "bucket handle" action of the ribs during respiration. The incessant motion of the rib cage transmits continuous stresses across the sternum. Thus, any method of closing a split sternum must be able to maintain compression and rigidity across the closure in the face of these constant stresses.

One technique used in the past involves closing the sternum with a plurality of spaced stainless steel wires. Five or more 20 gauge stainless steel wires are placed either parasternally (around the sternum) or transternally (through the sternum) using a large, swaged-on cutting needle. The needles are cut off and the sternal halves are approximated by twisting the wires. Finally the wires are cut short and the ends are tucked into the adjacent tissue.

While this is a useful surgical technique for closing the sternum, there are certain problems associated with this procedure. The wires are difficult to place and if to be placed transternally, the needle must be driven through the sternum, a very difficult task. The internal mammary artery is subject to being injured during the procedure. Also, the sharp wires often cause cutting of surgical gloves and may injure the surgeon. Twisting the wires while tightening may produce torsional stresses and may even severely weaken or fracture the wires. The stresses imparted by respiratory motion of the chest cage can further fatigue or break the wires. The wires may also slice through thin or osteoporotic bone. Hence, closure of the sternum with wires is a slow and tedious if not dangerous technique.

To overcome the drawbacks of conventional wire banding, it has been proposed to use a board in front of the sternum through which the wires pass. Others have suggested replacing the wires with various types of clamps or closures.

Presently, the best system seems to be to employ flat flexible stainless steel bands instead of wires. Each band may be formed integrally with a surgical needle at one end and a locking member at the other end. One type of such band is disclosed in U.S. Pat. No. 4,535,764 to Ebert. However, Ebert's locking member requires that the band be threaded through an opening in the locking member and bent back over the member and threaded through two other openings, a complicated and time consuming task. Another variation is disclosed in U.S. Pat. No. 4,730,615 to Sutherland. Sutherland uses a polymer coated metal band with an upstanding head. Adjacent the head is a serrated spine portion which is locked by a metal finger on a channel in the head.

A significant improvement over the assemblies taught by Sutherland and Ebert is the banding assembly disclosed in U.S. Pat. No. 4,813,416, issued to William Blasnik and Stanley Pollak. That banding assembly includes a locking member in the form of a buckle. The buckle has a loop segment under the saddle. The segment terminates in a spring tooth adapted to engaged an opening in the band when the band is pulled through a channel. The channel is defined by "C" shaped flanges extending upwardly from either side of the saddle.

In spite of the success of the band disclosed in U.S. Pat. No. 4,813,416, it too has certain drawbacks. The buckle is not flat because of the loop segment. However, the loop cannot be eliminated because as the band is pulled through the buckle, the buckle must be held by a clamp which engages the loop. Threading the band through the "C" flanges is sometimes difficult because of the shape of the buckle and rigidity of the flanges. Once the band is tighted, it must be trimmed. This may result in a tail with one or more sharp edges which are exposed.

U.S. Pat. No. 5,366,461 and U.S. Pat. No. 5,437,685 issued to William Blasnik teach a banding assembly which is an improvement over the band of U.S. Pat. No. 4,813,416 in that the structure of the buckle has been substantially revised to make it flat by eliminating the loop segment entirely and by providing new members in the form of upstanding ears with clamp receiving openings to permit the buckle to be held firmly by a towel clamp as the band is tighted.

The ears also serve another function. They are spaced in relation to the band width such that once the band is pulled through the channel, tightened, locked and trimmed, the remaining tail can be bent back over the buckle and snap-fitted between the ears to a position proximate the buckle floor such that it is safely tucked away. Crimping the ears over the tail insures that no sharp edges are exposed, permanently locks the band and at the same time, reduces the profile of the buckle.

The buckle in the patented Blasnik banding assembly, because it is the member which is engaged by the clamp as the band is pulled through the channel, subjected to a large amount of force. It is therefore necessary, in order to insure that the buckle does not separate from the band, that the buckle be affixed securely to the band. In the patented Blasnik banding assembly, the buckle was attached to the band with two elements which extend downward from the undersurface of the buckle and are received in openings provided in the band. Once in position the elements are bent toward each other.

The present invention improves upon this method of buckle attachment by providing two additional spaced tabs extending from the rear edge of the band. The tabs are bent around the edge of the buckle and to a position parallel to and adjacent with the buckle surface. The recess between the tabs preferably forms one of the element receiving openings.

It is, therefore, a prime object of the present invention to provide a buckle securing means for a sternum banding assembly which increases the strength of the connection between the buckle and the band, permits the application of relatively high forces on the buckle when securing the band.

It is another object of the present invention to provide a buckle securing means for a sternum banding assembly in which the recess between the securing tabs forms one of the band openings which received the downwardly extending elements from the buckle.

It is another object of the present invention to provide a buckle securing means for a sternum banding assembly which is simple in design and inexpensive, yet extremely reliable.

In accordance with the present invention, an assembly for banding the sternum is provided including an elongated flexible band having first and second ends. A needle is attached to the first end of the band. A buckle is attached proximate the second end of the band for receiving and locking the band. The buckle includes a surface and an edge. Means are provided for affixing the buckle to the second band end. The affixing means comprises tab means extending from the second band end and bent around the buckle edge to a position adjacent the buckle surface.

The tab means preferably comprises first and second spaced tabs. The first and the second tabs define a recess therebetween.

The band has first and second openings. The affixing means further comprises first and second elements extending from the buckle and adapted to be received in the first and second band openings, respectively. Preferably, the recess between the tabs forms one of the band openings.

The assembly is designed for use with a hand held clamp. Means are provided on the buckle for engagement with the clamp, permitting the buckle to be retained by the clamp, as the band is received in the buckle.

The means for engagement by the clamp includes a substantially upstanding element extending from the buckle surface and having an opening therein adapted to receive the clamp. Preferably, the means for engagement by the clamp comprises first and second substantially upstanding, spaced elements each having an opening therein adapted to receive the clamp.

To these and to such other objects are may hereinafter appear, the present invention relates to buckle securing means for a sternum banding assembly, as described in detail in the following specification and recited in the annexed claims, taken together with the attached drawings, wherein like numerals refer to like parts and in which:

FIG. 1 is a top plan view of the banding assembly of the present invention;

FIG. 2 is a side view of the banding assembly of FIG. 1;

FIG. 7 is a perspective view of the banding assembly showing the buckle retained by a towel clamp;

FIG. 8 is a perspective view of the buckle showing the band tail being placed and the ears being crimped;

Figure 3:
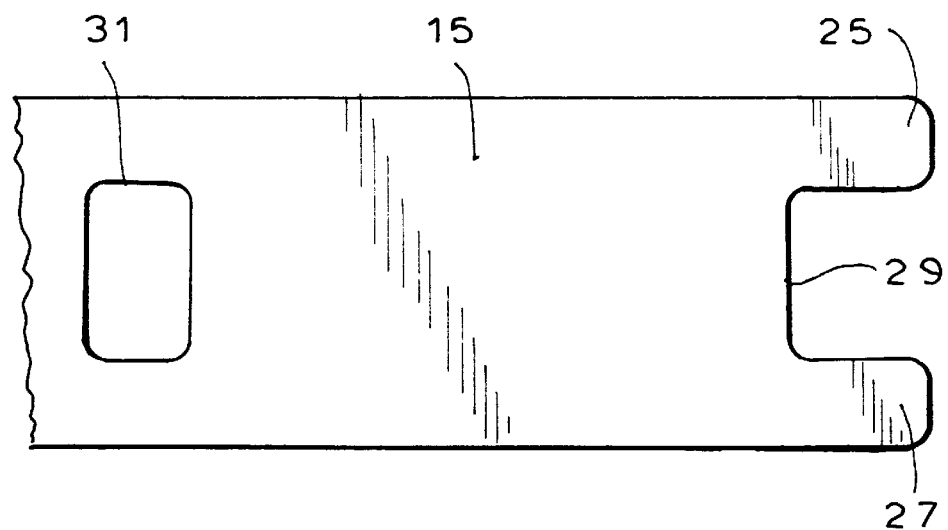
FIG. 3 is an enlarged top plan view of the end of the band showing the securing tabs.

FIGS. 9(a)–9(g) collectively illustrate the steps employed to band a split sternum with the banding assembly of the present invention.

As seen in FIGS. 1 and 2, the banding assembly includes an elongated, thin and relatively wide flat band 10, preferably made of stainless steel. A surgical needle 12 extends from one end of band 10. Needle 12 is preferably integral with the band but may be a separate part riveted or otherwise affixed to the band. Mounted proximate the other end of band 10 is a buckle 14.

Needle 12 is curved to facilitate insertion from one parasternal location, under the sternum halves and then outwardly at an opposite parasternal location. Adjacent needle 12 is a band section 16 of gradually increasing width. Section 16 has protrusions or ripples 18 on the top surface. Ripples 18 serve to gently expand the opening in the bone to permit the band to pass through, even when kinked or distorted.

Next to ripple section 16 is a relatively narrow section 19 which widens to the main band section 20. Situated proximate the connection between section 18 and 20 is a dome-shaped guide member 22 which extends above the band surface, preferably to the plane of the top surface of riples 18. Member 22 facilitates entry of the main section 20 of the band into the channel in buckle 14. Main section 20 has a plurality of spaced slots 24. Slots 24 are adapted to be engaged by the locking mechanism 37 in the buckle.

As seen in FIG. 3, the end 15 of band 10 opposite to that to which needle 12 is affixed is provided with two outwardly extending securing tabs 25, 27 spaced apart by a generally rectangular recess 29. Inwardly spaced from recess 29, but aligned therewith along the centerline of the band, is an opening 31.

Figure 4:
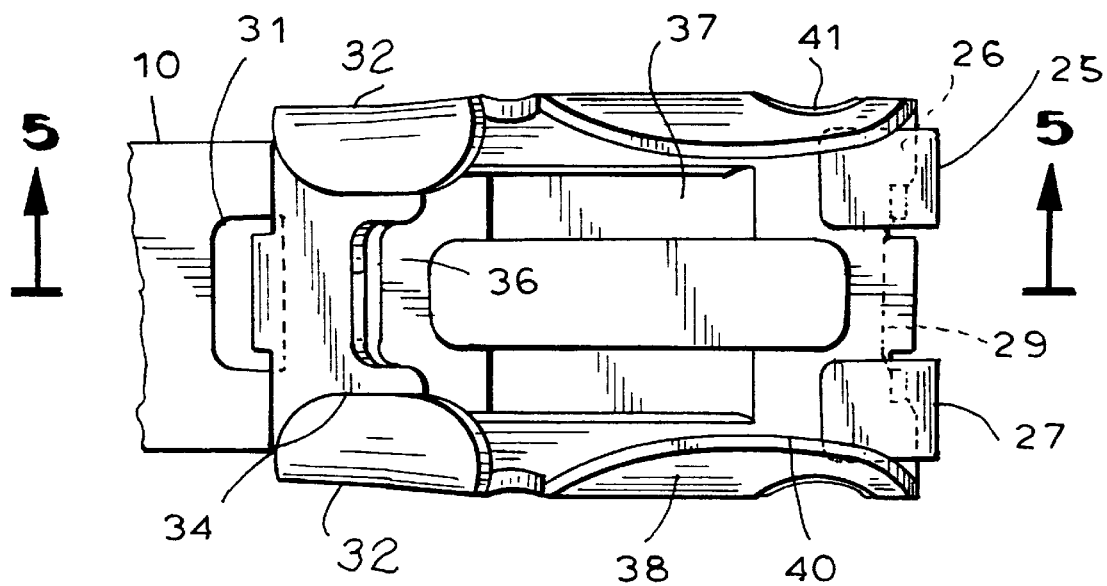
FIG. 4 is an enlarged top plan view of the buckle and band showing the securing tabs prior to bending.
Figure 5:
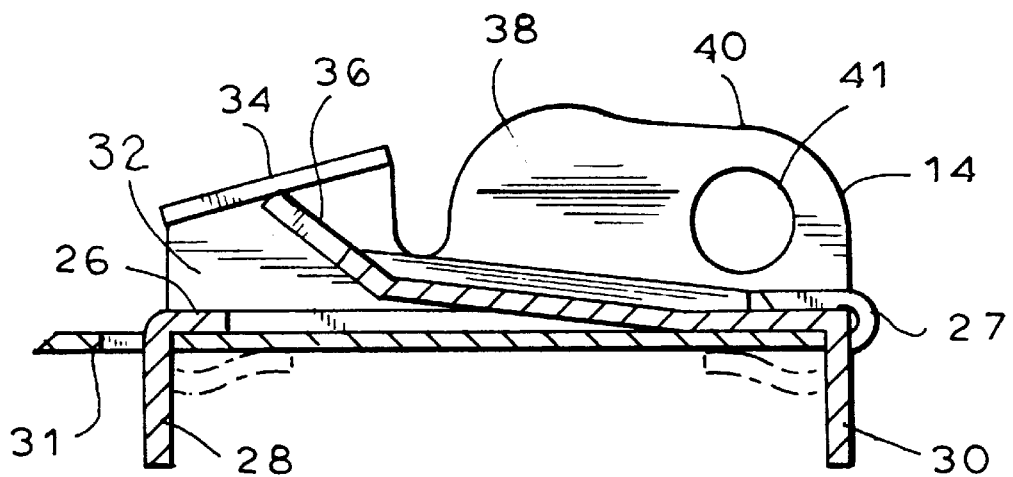
FIG. 5 is a side cutaway view of the buckle of FIG. 4, taking along line 5-5 with the securing tabs bent into position.
Figure 6:
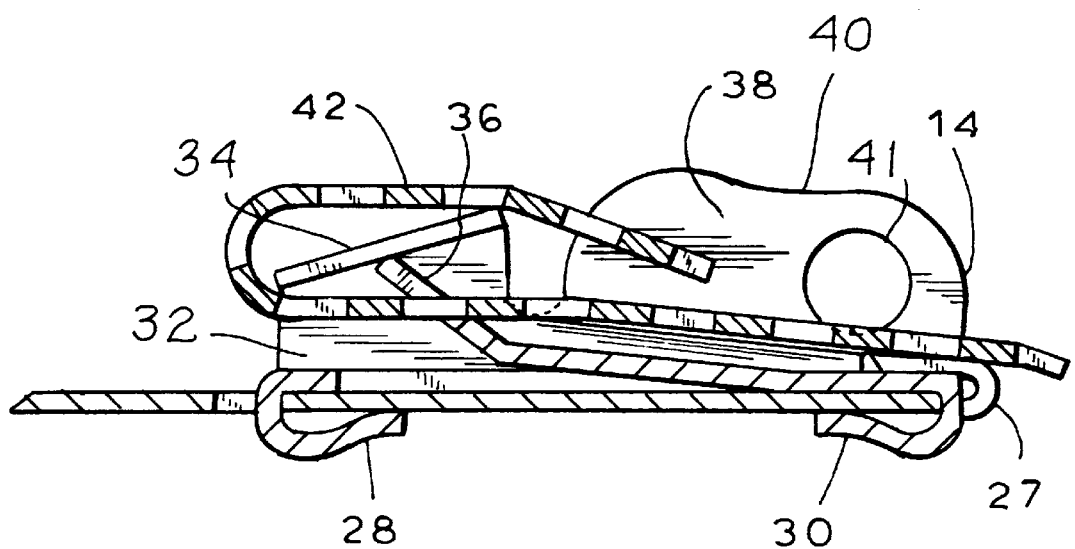
FIG. 6 is a side cutaway view of the buckle of FIG. 4, showing the band tail after crimping.

As best seen in FIGS. 4 and 5, the buckle 14 comprises a substantially planar floor 26 having downwardly extending elements 28, 30 at the forward and rear edge, respectively. Elements 28, 30 are adapted to extend through spaced openings 29, 31 near the end 15 of band section 20. Elements 28, 30 are bent inwardly to secure buckle 14 to band 10. Tabs 25 and 27 are then bent around the rear edge of buckle floor 26 until they are adjacent the buckle floor. These tabs substantially increase the strength of the connection between the band and buckle.

A pair of oppositely oriented spaced "C" shaped flanges 32 extend upwardly from opposite sides of floor 26, beginning at the forward end of the buckle and extending toward the rear for approximately one third of the length of the buckle. Flanges 32 are relatively thick and rigid and define the channel into which band 18 will be received. The inwardly extending top portions 34 of the flanges are inclined upwardly, away from floor 26. Thus, the channel is wedge shaped, being smallest at its mouth and gradually becoming larger toward the rear of the buckle.

Extending upwardly from floor 26, toward the plane of top portions 34, is a locking tooth 36. Tooth 36 is adapted to be received within one of the slots 24 in band 10 to lock and band in position within the channel defined by flanges 32.

Also extending from floor 26, at either side thereof, and substantially aligned with flanges 32 are a pair of upstanding ears 38. Ears 38 are slightly curved toward each other such that the top edges 40 of the ears are the points which are closest together. Edges 40 are spaced apart by a dimension which is slightly less than the width of band section 20. The flexibility of the stainless steel material of which ears 38 are made permits a section of the band to "snap-fit" between the ears as explained below.

Ears 38 are each provided with openings 41, shaped and sized to accept the moveable arms of a conventional towel clamp. Thus, the buckle can be engaged and retained by the arms of a towel clamp as the band is pulled through the channel and tightened into the locking position such that tooth 36 protrudes into one of the slots 24 in the band.

Ears 38 serve the additional purpose of permanently retaining the tail 42 of the band, after it has been trimmed, in close face to face relation with spring element 37, in a way which covers any sharp edges of the band which may result from trimming the tail. Once the band is locked in position in the channel, it is trimmed to have a tail with a length about as long as the buckle. The tail is bent back over flanges 32, toward the rear of the buckle, and "snap fits" between ears 38. Ears 38 are then crimped inwardly, covering the edges of the tail band. In this way, sharp or jagged edges are protected and a low profile is achieved.

The method of using the banding assembly of the present invention is illustrated in FIGS. 9(a)–9(g) which show the various operations involved. When the sternum is ready to be closed, needle 12 is threaded through or around the sternum sections, as shown in FIG. 9(a). Hemostats or needle holders are used to manipulate the band and needle. Once the band is in place (FIG. 9(b)), the needle 12 is cut off, about an inch from narrow section 18. The narrow section 18 is then inserted between flanges 32 and dome-shaped member 22 guides the main section 20 of the band into the channel (FIG. 9(c)). A clamp is used to pull the band tight while the buckle is retained by a towel clamp whose arms are received in openings 41 (FIG. 9(d)). Once the band is in position, tooth 36 lodges in one of the slots 24 urged upwardly by spring element 37, to lock the band within the channel. The band is bent upwardly, 90° from floor 26 of the buckle and trimmed to form a tail 42, approximately 4 slots long (FIG. 9(e)).

Tail 42 is bent back over the buckle and particularly over flanges 32 and "snap fit" between ears 38 as illustrated in FIG. 9(f). Ears 38 are crimped to overlap the edges of the tail. (FIG. 9(g). In this way, the tail is permanently retained within the buckle and no sharp edges are exposed.

The entire procedure can be performed quickly and efficiently, using only conventional operating room instruments. The resulting structure has a low profile, with no protruding parts or sharp edges. However, the band is reliably locked by the tooth and held securely by the folded tail 42.

It should now be appreciated that the present invention relates to buckle securing means for a sternum banding assembly in which spaced securing tabs are bent around the rear edge of the buckle into a position adjacent the floor. The recess between the tabs preferably forms one of the openings in the band adapted to receive downwardly extending elements. In this way, the strength of the connection between the buckle and band is substantially enhanced.

While only a single preferred embodiment of the present invention has been disclosed for purpose of illustration, it is obvious that many variations and modifications could be made thereto. It is intended to cover all of these modifications and variations which fall within the scope of the invention, as defined by the following claims.

I claim:

1. An assembly for banding the sternum comprising an elongated flexible band having first and second ends, a needle at said first end of said band, a buckle proximate said second end of said band for receiving and locking said band, said buckle comprising a surface and an edge, and means for mounting said buckle to said second band end in a fixed position, said mounting means comprising first and second spaced tabs extending from said second band end and bent around said buckle edge to a position substantially adjacent said buckle surface.

2. The assembly of claim 1 wherein said first and said second tabs define a recess therebetween.

3. The assembly of claim 2 wherein said band has first and second openings and wherein said mounting means further comprises first and second elements extending from said buckle and adapted to be received in said first and second band openings, respectively.

4. The assembly of claim 3 wherein said recess comprises one of said first and second band openings.

5. The assembly of claim 1 for use with a hand held clamp, further comprising means on said buckle for engagement with the clamp, permitting said buckle to be retained by the clamp as said band is received in said buckle.

6. The assembly of claim 5 wherein said means for engagement by the clamp comprises a substantially upstanding element extending from said surface and having an opening therein adapted to receive the clamp.

7. The assembly of claim 5 wherein said means for engagement by the clamp comprises first and second substantially upstanding, spaced elements each having an opening therein adapted to receive the clamp.

8. The assembly of claim 7, wherein said band has an end section and further comprising means adapted to cover said band end section after said band is locked, said covering means comprising said upstanding elements.

9. An assembly for banding for sternum comprising an elongated flexible band having first and second ends, a needle at said first end of said band, a buckle proximate said second end of said band for receiving and locking said band, said buckle comprising a surface and an edge, and means for mounting said buckle to said second band end, said mounting means comprising tab means extending from said second band end and bent around said buckle edge to a position substantially adjacent said buckle surface, said tab means comprising first and second spaced tabs, said first and said second tabs defining a recess therebetween, said band having first and second openings, said mounting means comprising first and second elements extending from said buckle and adapted to be received in said first and second band openings, respectively.

10. The assembly of claim 9 wherein said recess comprises one of said first and second band openings.

11. The assembly of claim 9 for use with a hand held clamp, further comprising means on said buckle for engagement with the clamp, permitting said buckle to be retained by the clamp as said band is received in said buckle.

12. The assembly of claim 11 wherein said means for engagement by the clamp comprises a substantially upstanding element extending from said surface and having an opening therein adapted to receive the clamp.

13. The assembly of claim 11 wherein said means for engagement by the clamp comprises first and second substantially upstanding, spaced elements each having an opening therein adapted to receive the clamp.

14. The assembly of claim 13, wherein said band has an end section and further comprising means adapted to cover said band end section after said band is locked, said covering means comprising said upstanding elements.

* * * * *